United States Patent [19]

Katsumoto et al.

[11] 4,132,670

[45] Jan. 2, 1979

[54] METHOD OF PREPARING VANADIUM (IV) PHOSPHATE COMPOSITION WITH HIGH INTRINSIC SURFACE AREA

[75] Inventors: Kiyoshi Katsumoto, El Cerrito; David M. Marquis, Lafayette, both of Calif.

[73] Assignee: Chevron Research Company, San Francisco, Calif.

[21] Appl. No.: 729,920

[22] Filed: Oct. 6, 1976

Related U.S. Application Data

[63] Continuation of Ser. No. 521,604, Nov. 6, 1974, abandoned, which is a continuation of Ser. No. 290,049, Sep. 18, 1972, abandoned.

[51] Int. Cl.$^2$ ............................................. B01J 27/18
[52] U.S. Cl. .................................... 252/437; 423/305; 260/346.75
[58] Field of Search ................ 423/305, 306; 252/437; 260/346.8 A

[56] References Cited

U.S. PATENT DOCUMENTS

| | | | |
|---|---|---|---|
| 3,156,706 | 11/1964 | Kerr | 252/437 X |
| 3,156,707 | 11/1964 | Kerr | 252/437 X |
| 3,864,280 | 2/1975 | Schneider | 252/437 X |
| 3,975,300 | 8/1976 | Burress | 252/437 X |

*Primary Examiner*—Patrick Garvin
*Attorney, Agent, or Firm*—D. A. Newell; John Stoner, Jr.; A. T. Bertolli

[57] ABSTRACT

A crystalline vanadium (IV) phosphate composition having an intrinsic surface area in excess of 10 square meters per gram is prepared by the reaction of orthophosphoric acid with a vanadium (IV) oxycompound. The vanadium compound is suspended in a suitable hydroxylic organic medium, for example isobutanol, and contacted with the acid at a temperature in the range 20° C. to 210° C. until the conversion is completed.

6 Claims, No Drawings

METHOD OF PREPARING VANADIUM (IV) PHOSPHATE COMPOSITION WITH HIGH INTRINSIC SURFACE AREA

CROSS-REFERENCE TO RELATED APPLICATIONS

This is a continuation of application Ser. No. 521,604, filed Nov. 6, 1974, now abandoned, which in turn is a continuation of application Ser. No. 290,049, filed Sept. 18, 1972, now abandoned.

BACKGROUND OF THE INVENTION

1. Field of the Invention

This invention relates to an improved process for the preparation of hydrocarbon oxidation catalyst compositions. More particularly, it relates to a new vanadium (IV) phosphate having a substantially improved intrinsic surface area and to a novel method for its production. Still more particularly, it relates to the production of maleic anhydride from n-butane in a vapor phase process employing the foregoing phosphate catalyst.

2. Prior Art Description

The preparation of mixed oxide compositions of vanadium and phosphorus and the use of these compositions as catalysts in hydrocarbon oxidations is known in the art. The conventional preparative methods are unsatisfactory in that:

(1) they usually require that the process equipment be fabricated of special corrosion-resistant materials of construction; and (2) they are troubled by serious waste disposal problems.

These difficulties arise from the employment of hydrogen chloride or oxalic acid for the dissolution of the vanadium component.

The known mixed oxide compositions, in general, suffer from a number of disadvantages which include relatively poor selectivities and activities as catalysts in the partial oxidation of a saturated hydrocarbon feed, for example n-butane to maleic anhydride, and the like oxidations with molecular oxygen.

Representative descriptions in the art which relate to the production of maleic anhydride from n-butane include U.S. Pat. No. 3,293,268.

THE INVENTION

A new and improved method for the preparation of vanadium (IV) phosphate compositions has now been found. The compositions are composed of vanadium, phosphorus (V) and oxygen; they have the following combination of characteristics:

(1) an intrinsic surface area in the range 10 to 100 square meters per gram (BET Method);

(2) a phosphorus to vanadium atomic ratio of about 1 to 1; and (3) an average valence for the vanadium in the composition in the range plus 4.0 to plus 4.5.

The compositions are prepared by the reaction of orthophosphoric acid with a vanadium-containing feed. The reactants are contacted in a suitable and substantially anhydrous hydroxylic organic liquid medium in a heterogeneous reaction mixture in which the vanadium-containing feed is a suspended particulate solid which is dispersed in the liquid and the phosphoric acid is dissolved in the medium. The reaction is effected at a temperature in the range 20° C. to 210° C., and at a pressure sufficient to maintain the liquid medium. The reaction temperature is maintained for a period sufficient for the conversion of the feed and in the range from 1 to 50 hours. For each liter of the medium an amount of vanadium in the range 0.1 to 5 gram atoms should be present in the mixture, and for each gram atom of vanadium, the mixture contains an amount of orthophosphoric acid in the range of 1.0 to 1.5 mols.

The vanadium-containing feeds suitable for use in the process are those which contain one or more compounds composed:

(1) of vanadium and oxygen; or (2) of vanadium, oxygen and hydrogen; or (3) of vanadium, oxygen, hydrogen and carbon.

These compounds should have an average vanadium valence (oxidation state) in the range 4.0 to 4.6.

The liquid media satisfactory for use in the process are substantially unreactive hydroxylic organic compounds which contain one or more primary or secondary hydroxyl groups, preferably one or two hydroxyl groups. They are therefore composed of carbon, hydrogen and oxygen and preferably have a carbon atom content in the range from 1 to about 20. The medium may also contain up to about 60 percent of an inert diluent such as a hydrocarbon, a chlorinated hydrocarbon, a chlorocarbon, an ether, or a mixture of the foregoing. Preferably the diluent compounds have a carbon atom content below about 15. At least about 40 percent of the liquid medium should consist of oxygen-containing organic compounds.

When the reaction is completed, the resulting heterogeneous liquid-solid mixture is separated into a solid fraction and a liquid fraction. The collected solid is subjected to further process treatments and the liquid may be recycled to the process or discarded as desired. After removal from the collected solid of the volatile material by drying at a temperature in the range 50° C. to 150° C., the solid is activated by heating at a temperature in the range 360° C. to 600° C.

Surprisingly, the present suspension process and the heterogeneous reaction mixture results in the production of a solid crystalline product which has a remarkably high intrinsic surface area. The product for practical purposes appears to be homogeneous. Contrary to the products obtained by conventional solution methods, in the present process the relative amount of phosphorus to vanadium in the product does not vary depending upon the ratio of reactants in the reaction mixture. Thus, and although a substantial excess of phosphoric acid is present in the reaction mixture, the product, nevertheless, has essentially a 1:1 atomic ratio of phosphorus to vanadium, i.e., within the range of 0.9:1 to 1.1:1 as measured by neutron activation analysis. This fact, as well as other factors to be considered below, are believed to establish that the present composition is essentially a unique compound rather than one which is but a mixture of vanadium and phosphorus oxides, the description usually given the resulting product obtained from conventional solution reaction systems. On the other hand, although most of the vanadium component in the present product appears to be of the plus 4 oxidation state, the average or mean valence of the compound varies in the range 4.0 to 4.5. Therefore, by the description vanadium (IV) phosphate, as used herein, is meant by definition that at least 50 percent of the vanadium component is of the plus 4 valence state.

The advantages of the present process include, in particular, the avoidance of the serious corrosion problems ordinarily experienced in previous processes requiring the presence of halogen or oxalic acids. It also avoids the necessity of evaporating a substantial amount of solvent as is required in the ordinary solution methods. These and other advantages will be appreciated from the description and examples below.

By intrinsic surface areas, as used in the specification, is meant by definition the surface area (BET Method) of the material of reference of itself, i.e., per se, and in the absence of a support, carrier or extender. By the BET Method, as used herein, is meant by definition the method of Messrs. H. Brunauer, P. H. Emmett and E. Teller, as described in J.A.C.S., Volume 60, 309 (1938).

By the term relatively unreactive, or the term inert, as used herein, having reference to a component of the liquid medium is meant by definition:
(1) that the compound does not set (polymerize) or decompose when in contact with phosphoric acid at the temperature of use; and
(2) as a practical matter, little or none of the compound reacts with phosphoric acid at the temperature of use.

EMBODIMENT

In a preferred embodiment a vanadium (IV) oxycompound is first prepared as a precursor of the desired phosphate. To this end, dry, powdered vanadium pentoxide and a mixture of isobutyl alcohol and benzyl alcohol are charged to a reactor fitted for stirring and with a reflux condenser and an associated water trap. For each formula ($V_2O_5$) weight in grams of the oxide, about 350 ml. of isobutanol and 2.2 mols of benzyl alcohol are charged to the reactor. The reactor and charge are then heated to the reflux temperature (about 120° C.) and this temperature is maintained until the color of the suspended solid turns black. Usually the time required for this change is from 5-8 hours. The average valence of the vanadium in the precursor is about +4.5 (as determined by magnetic susceptibility measurements) and thus the vanadium component is roughly 50% vanadium (IV) and 50% vanadium (V). The water formed during the partial reduction of the vanadium pentoxide as a result of the above treatment may be removed from the reaction mixture by azeotropic distillation and collected in the water trap.

In a separate vessel a solution of anhydrous 100% orthophosphoric acid in isobutanol (2.0 mols of the acid in about 350 ml. of isobutanol) is prepared.

After removing the water from the black slurry of partially reduced vanadium pentoxide in isobutanol and cooling of the resulting slurry to a temperature in the range of from about 20° C. to about 50° C., the orthophosphoric acid-isobutanol solution at about 25° C. is added to the slurry, and the mixture is then heated to the reflux temperature and maintained at this temperature until reaction occurs as indicated by change in the color of the solid, for example from black to blue. The time required for this change is usually in the range 0.5 to 5 hours. During this heating period, any water formed is removed by azeotropic distillation. Heating may be continued for at least 12 more hours without damage to the catalyst. Total heating time should be sufficient to convert the vanadium in the solid to an average oxidation state in the range of 4.0 to 4.3.

The resulting vanadium (IV) phosphate, a solid suspended in the isobutanol medium, is separated from the suspension liquid by filtration. Depending upon the desired form of the ultimate activated catalyst, it is handled in a variety of the ways customarily employed in the catalyst art. For a fixed bed catalyst use it is either pelleted and dried or extruded and dried. Where the extruded form of the catalyst is desired, sufficient of the original suspending liquid is retained or added to the solid for convenient handling and processing during the extrusion, i.e., about 20 weight percent of liquid based upon the dried solid, and the extruded material is dried as before. The drying is usually effected at about 150° C. while passing a stream of air through the drying material.

For the activation of the precipitated vanadium (IV) phosphate, the following schedule is carried out:
(1) The dried solid is heated to 380° C. in a stream of air flowing at 1.5 vol/vol/min. The heat input should yield a rate of temperature increase of about 3° C. per minute.
(2) The 380° C. temperature is then maintained and the same air flow rate continued for about 2 hours.
(3) The temperature is then increased from 380° C. to 480° C. at the 3° C. per minute rate of increase while passing in air-butane mixture, 1.5 volume percent of butane in air, through the bed (12½ inch by ¾ inch diameter tube) at a flow rate of 2-3 vol/vol/min.
(4) The 480° C. temperature is maintained for about 15 hours while continuing the air-butane flow rate as before.
(5) The temperature is then reduced from the 480° C. value to 420° C. and the air-butane flow rate is increased to a VHSV of 1,000 hrs.$^{-1}$ (17 vol/vol/min.).
(6) Finally the temperature is adjusted upward or downward, as required, to achieve the desired degree of butane conversion.

Usually the performance of the catalyst stabilizes after a short run of about 100 hours. The activated catalyst has a standard activity, K at 800° F., (see discussion below) which is usually of the order of 3000 and higher, has an intrinsic surface area of 18 $m^2/g$ and higher, and a selectivity of above 60 mol percent for the conversion of an n-butane feed to maleic anhydride under suitable oxidation conditions.

THE LIQUID ORGANIC MEDIA

The organic compounds satisfactory for use as liquid media in the process must be composed of carbon, hydrogen and oxygen having no olefin double bonds and having a carbon atom content in the range of 1 to 20, preferably 1 to 10. Included in this category are alcohols, aldehydes, ketones, and ethers. Both mono and polyfunctional compounds may be used. In addition to serving as a liquid dispersion medium for the solid feed, these organic compounds function as solvents or diluents for the phosphoric acid. The acid must be in a diluted stage at the reaction stage; otherwise, the resulting product is a cement-like material which has a low intrinsic surface area. In general, the useful organic compounds must be relatively unreactive towards phosphoric acid.

Alcohols

The preferred organic compounds are the primary and secondary alcohols. Alcohols which contain 1, 2, or 3 hydroxyl substituent groups are especially preferred because these, in general, are readily liquefied at useful temperatures in the process range. Representative hydroxylic compounds useful in the process include monoalcohols such as: methanol, ethanol, 1-propanol, 2- propanol, 1-butanol, 2-butanol, 2-methyl-1-propanol, 1-pentanol, cyclohexanol, 1-octanol, 2-octanol, 3-octanol, 4-octanol, 2-hexadecanol, 2-eicosanol, 2-ethyl-1-hexanol, benzyl alcohol, etc., dialcohols such as: ethylene glycol, 1,4-butanediol, 1,2-propanediol, etc., trialcohols such as glycerine, 2,2-dimethylol-1-propanol, etc., ether alcohols such as: diethylene glycol, triethylene glycol, 2-butoxyethanol, 4-methoxybutanol, tetrahydrofurfuryl alcohol, etc.

Aldehydes and Ketones

Representative aldehydes include benzaldehyde, acetaldehyde, propionaldehyde, m-tolualdehyde, 2-ethylhexanal, etc. Representative ketones include acetone, methylethylketone, cyclohexanone, diethyl ketone, dibutyl ketone, methyl isopropyl ketone, methyl sec.butyl ketone, benzophenone, etc.

Ethers

Representative ethers include diethyl ether, dibutyl ether, tetrahydrofuran, anisole, dioctyl ether, 1,2-dimethoxyethane, 1,4-dimethoxybutane, etc.

The primary and secondary alkanols (ROH) having a carbon atom content in the range from 3 to 6 are a preferred class of hydroxylic compounds for reason of cost and availability and because of their convenient boiling points.

THE VANADIUM-CONTAINING FEED

Compounds of vanadium and mixtures of compounds of vanadium in which the vanadium has an average valence (oxidation state) in the range 4.0 to 4.5 and which are composed of:
 (1) vanadium and oxygen;
 (2) vanadium, oxygen and hydrogen; or
 (3) vanadium, oxygen, hydrogen and carbon
are, in general satisfactory feeds for the instant process and are contemplated for use herein.

Vanadium pentoxide is usually the commercially available form of oxidized vanadium, and thus it is employed in an embodiment of the invention as a precursor for the production of a feed containing vanadium of the desired average valence. In the embodiment, vanadium pentoxide is dispersed in a hydroxylic organic liquid medium, as described above, except that no phosphoric acid is included. The mixture of liquid and solid is heated and maintained at a temperature in the range 20° C. to 200° C. until the average valence of the vanadium changes to a value in the range plus 4.0 to 4.6. This change occurs over a range of time, usually in the range 1 to 50 hours, depending upon the temperature employed and the hydroxylic medium. The reduction of the vanadium is accompanied by the oxidation of an equimolar amount of the medium and some water is also formed. The reduction of vanadium in the plus 5 oxidation state by the use of organic compounds (conversely the oxidation of organic compounds by vanadium in the plus 5 state) is well known in the art (see, for example, "Oxidation of Organic Compounds With Quinquivalent Vanadium," by J. S. Littler and W. A. Water, J.C.S., 1959, Pages 1299–1305), and is not of itself novel.

To facilitate the desired reduction of the vanadium, for example to reduce the time required for the reduction, an active organic compound in the oxidation-reduction sense is desirably employed in the mixture of vanadium pentoxide and hydroxylic liquid medium. For example, isobutanol, benzyl alcohol, formaldehyde, methyl ketones, aldehydes, and the like are readily oxidized by vanadium pentoxide and are useful herein for the adjusting of the average valence of the vanadium to the desired range. The resulting mixture may be used as the source of the vanadium feed and of the medium for the present process. Preferably, the water which is produced as a coproduct of the oxidation-reduction reaction is removed from the medium prior to the addition of the orthophosphoric acid required for the conversion of the vanadium oxysalt to the desired vanadium (IV) phosphate.

The oxidation state of the vanadium compounds herein is determined by conventional methods.

Representative vanadium-containing compounds satisfactory for use in the process include vanadium tetroxide, vanadium oxysulfate, oxyvanadium (IV) carboxylate salt, vanadium oxyacetylacetonate complex or partially reduced vanadium pentoxide, ammonium metavanadate or vanadic acid, and the like. The polarity of the medium may be adjusted (i.e., by selection of a suitable hydroxylic acid) to limit solubility sufficiently that only a minor solubility (less than 10 weight percent of the medium) ensures maintenance of the required solid phase and dispersion of the feed. A limited solubility (up to a 10 weight percent) is probably beneficial in that mass transfer from the solution and crystal orientation effects may be accelerated in this case.

Inert diluents may be included as a component of the liquid medium of the process for a number of reasons which include:
 (1) to facilitate removal of water from the medium by azeotropic distillation;
 (2) to partially replace more costly hydroxylic liquid components; and
 (3) to reduce the polarity of the reaction medium.

The liquid medium essentially must be an organic hydroxylic solvent for the orthophosphoric acid reagent employed in the process. Accordingly, at least about 40 volume percent of the medium should be composed of the hydroxylic organic compounds described above. The liquid medium must also be a substantially anhydrous liquid medium for the reason that water, when present in excess, has a leveling (reducing) effect upon the intrinsic surface area of a vanadium (IV) phosphate. The amount of water which can be present in the medium varies depending upon the particular hydroxylic compounds included in the medium and upon the reaction temperature used. In general, the amount of water which can be present without an undue leveling effect upon the intrinsic surface area and related properties of the desired vanadium (IV) phosphate will be in the range 0 to 2 mols per mol of phosphoric acid. Thus, in terms of a liquid reaction, this amount corresponds to a substantially anhydrous liquid medium. Preferably, the medium is anhydrous. Further, since a liquid medium is required, the reaction will be carried out at a pressure (a dependent variable) sufficient to maintain the liquid phase.

REACTION VARIABLES

Temperature-Time

The usual considerations apply; that is, higher temperature-shorter times. The reaction can be carried out over a range of temperature and the time required varies in the range 1 to 50 hours depending upon the temperature. The shorter times correspond with the employment of the higher temperatures. At about 213° C., anhydrous orthophosphoric is converted to polyphosphate species and these are undesirable. Accordingly, the temperature should be below about 210° C. As a practical matter, the use of a reaction temperature below about 20° C. is undesirable, because the time to achieve a satisfactory conversion is relatively long. Preferably, the reaction temperature is in the range from 80° C. to 150° C.

Feed Sizing

The vanadium-containing feed should be introduced into the liquid medium as a particulated solid. Otherwise, the time required to complete the conversion of the feed to a useful vanadium (IV) phosphate product is impracticably long. In general, a particle sizing of the feed to one in the range below 10 millimeters average diameter is desirable. As a practical matter, a feed sizing in the range 1 to 0.1 mm. is preferred.

INTERMEDIATE PROCESSING

Separation

The reaction product mixture is a heterogeneous liquid-solid mixture of which the solid is the desired vanadium (IV) phosphate. Ordinary methods, filtration, centrifugation, decantation and the like, are satisfactory means for carrying out the separation.

Drying

Some liquid, whether occluded or absorbed, usually remains with or in the collected solid. For its removal a drying stage is required. The drying may be accomplished over a wide range of temperature, i.e., from about 50° C. to 350° C., at an atmospheric or a reduced pressure. At about 370° C. the vanadium (IV) phosphate loses about 1 mol of water per gram atom of phosphorus and undergoes a crystal-phase transition. The ultimate activity of the vanadium (IV) phosphate depends in large part upon the manner in which the first and a second activating conditioning is carried out. Therefore, the drying must be effected reasonably below the aforementioned crystal phase transition temperature, i.e., below about 350° C., preferably at 150° C. The dried composition has an intrinsic surface area which, in general, exceeds 10 square meters per gram.

The dried solid is readily adapted to standard catalyst preparation procedures and the order used for the several stages is not particularly significant. It may be subjected to grinding, sizing, slurrying in a suitable liquid medium (e.g., a hydroxylic liquid as described above or water), and extruding. The usual considerations and requirements, as known in the oxidation catalyst art, apply re the sizing and the shaping of the particulated or extruded catalyst materials herein for the conversion of the dried vanadium (IV) phosphate for use as an oxidation catalyst.

Activation

Where the vanadium (IV) phosphate is to be employed as a fixed or fluid bed catalyst for the partial oxidation of n-butane to maleic anhydride, the relative activity and selectivity of the phosphate is severely dependent upon the activation procedure which is applied to the dried solid. However, once through the activation stage, the resulting vanadium (IV) phosphate composition is stable and has a long, useful life.

The activation was carried out by heating the vanadium phosphate in air followed by heating the product in hydrocarbon and air mixture at an elevated temperature. More specifically, the dried vanadium (IV) phosphates were charged to a fixed bed vessel and heated to 380° C. at a moderate rate in a flowing stream of air which passed through the bed at 2-3 volume per volume per minute. After 2 hours at temperature and this air flow rate, the air stream was replaced by an n-butane-air (1.5 volume percent n-butane) stream flowing at the 2-3 V/V/min. rate and the temperature was again increased at a moderate rate to 480° C. This condition was maintained for about 15 hours. The temperature was then lowered to 420° C. The space velocity (VHSV) was increased to 1000 hr.$^{-1}$ (17 V/V/min. at S.T.P.) and the temperature in most cases was adjusted until the conversion of the n-butane was 90 percent.

The activity of various catalyst compositions for oxidation of hydrocarbons, more specifically n-butane, was determined by tests in a $\frac{3}{4}$ inch by $12\frac{1}{2}$ inch reactor in which n-butane was oxidized to maleic anhydride at about 90% conversion. The catalyst activities are expressed as the relative first order rate constant, K, corrected to 800° F. average bed temperature, and calculated as follows:

$$K = \frac{\frac{T}{535}}{\frac{P}{14.7}} \times VHSV \times Ln\frac{1}{1-x}$$

$T$ = Average bed temperature (° R)
$P$ = Average bed pressure (atm.)
$VHSV$ = Vapor hourly space velocity
$= \frac{\text{Volume of feed gas (75° F, 1 psia.)}}{\text{Volume of reactor bed} \times \text{hr}}$
$x$ = Mole fraction n-butane converted The K at the reaction temperature is then corrected to 800° F. by the following equation:

$$K_{800} = K_T e^A$$

in which $$A = 16.54\,(1260 - T/T)$$

Values of K in excess of 2000 are considered very satisfactory, and values in excess of 1000 are considered to exceed the activity of the prior art catalysts. For completely satisfactory catalysts it is necessary that, in addition to having high activities (K values), they must also convert a substantial amount of the feed stock to product. That is, they must have high selectivity for producing the desired product. Such selectivities are measured as the mols of product produced per mol of reactant consumed, usually expressed as mol percent.

The following examples are offered in further illustration of the invention. Unless otherwise specified, the proportions are on a weight basis.

EXAMPLE 1

A 2-liter flask equipped with a mechanical stirrer, a condenser with a Dean-Stark water trap, a thermometer and an addition flask was charged with 182 grams (1.0 mol) of vanadium pentoxide and 820 ml of isobutyl alcohol. The contents were heated at reflux for 3 hours, during which time 2 ml. of water were collected in the trap. Then 277 grams (2.4 mols) of 85% phosphoric acid was added slowly and the reaction temperature maintained at the reflux for 6 additional hours during which time 24 ml. of water were removed.

After standing at room temperature for 60 hours, the reaction mixture was heated at reflux for 7 hours, during which time $2\frac{1}{2}$ ml. of water were removed from the reaction vessel. After standing for 20 hours at room temperature, the solvent was removed by distillation from the slurry to leave 413 grams of a blue solid which was ground to less than 20 mesh.

To 150 grams of this powder there was added 35 grams of water. The resulting paste was extruded to form pellets ⅛ inch in diameter and about ¼ inch long. The pellets were dried in an oven at 150° C. for 2 hours.

The catalyst pellets were charged to a vertically mounted fixed bed reactor tube ¾" by 12". Activation of this catalyst was accomplished by first heating the pellets in a stream of air at 380° C. for 2 hours. Then the temperature was slowly raised to 480° C. over a period of 1 hour, during which time a 1.5% butane in air mixture was passed over the catalyst. Heating was continued at 480° C. for about 15 hours in the presence of an air-butane mixture. Analysis by a magnetic susceptibility measurement showed an average vanadium oxidation state of +4.2.

Then an air-n-butane mixture was passed through this reactor at an average bed temperature of 446° C. Maleic anhydride was recovered by cooling from the exit gas stream. After 193 hours on stream, the activity value of $K_{800}$ was 2200 and the selectivity was 47%.

EXAMPLE 2

In an apparatus similar to that used in Example 1, 154.5 grams (0.85 mol) of vanadium pentoxide was slurried in a mixture of 600 ml. of isobutyl alcohol and 400 ml. of benzyl alcohol. The resulting mixture was stirred at the reflux for 5 hours. A portion of the resulting black suspension was analyzed as having an average vanadium oxidation state of +4.45 by a magnetic susceptibility measurement.

The slurry was cooled to 60° C. and 200 grams (2.04 mols) of 100% orthophosphoric acid in 200 ml. of isobutyl alcohol was added slowly. The resulting mixture was stirred at reflux for about 20 hours. After cooling to room temperature, the solid was removed by filtration, dried to about 20% (wt.) of solvent and extruded in the form of ⅛" diameter pellets. These pellets were dried by heating at 150° C. for 2 hours. Activation was by the same procedure as described in Example 1.

These pellets were then used to catalyze the air oxidation of n-butane to maleic anhydride. After 488 hours on stream the catalyst had an activity constant $K_{800}$ of 4085. The selectivity was 44 mol percent at 90% butane conversion.

EXAMPLE 3

The procedure of Example 2 was followed except that the quantity of benzyl alcohol was 200 ml. instead of 400 ml. In this case a catalyst was obtained which had a surface area of 28 m²/gram, a vanadium:phosphorus mol ratio of 1:1, and an average vanadium oxidation state of about +4.15. In the air oxidation of n-butane to maleic anhydride, this catalyst had a $K_{800}$ activity value of 3400 and a selectivity of 66%.

EXAMPLE 4

The procedure of Example 2 was followed except that isopropyl alcohol was used in place of isobutyl alcohol. This catalyst had a $K_{800}$ activity value of 2050 and a selectivity of 46%.

EXAMPLE 5

The procedure of Example 3 was followed except that after refluxing the vanadium pentoxide slurry for 16 hours, it was cooled to room temperature and 200 ml. of benzene added. Then 235 grams (2.04 mol) of 85% phosphoric acid was added dropwise at a rate sufficient to maintain reflux. After this addition, refluxing was continued and a benzene-water azeotrope was removed through a Dean-Stark trap until no more water evolved. Then the benzene was distilled off and the alcoholic slurry refluxed for about 16 hours. This catalyst had a surface area of 25 m²/gram, a vanadium:phosphorus mol ratio of 1:1, and an average vanadium oxidation state of about +4.15. In the catalytic air oxidation of n-butane, this material had a $K_{800}$ of 1667 and a selectivity of 55%.

EXAMPLE 6

In this example, 154.5 grams (0.85 mol) of $V_2O_5$ was refluxed in 800 ml. of benzyl alcohol for 2½ hours. Then, after cooling, 235 grams (2.04 mol) of 85% phosphoric acid was added, and the resulting mixture was stirred and refluxed for about 16 hours. No attempt was made to remove water from the reaction mixture. Product work-up was the same as before. In this case $K_{800}$ was 750 and selectivity was 43%.

EXAMPLE 7

The same apparatus as described above was charged with 154.5 grams (0.85 mol) of $V_2O_5$, and 400 ml. of n-amyl alcohol. To this slurry 38 grams of glycerine was added slowly. The mixture was refluxed for 16 hours with azeotropic removal of n-amyl alcohol and water. Then 235 grams (2.04 mol) of 85% phosphoric acid was added and the resulting mixture was refluxed for 16 hours, during which time 50 ml. of water was removed. The resulting slurry was worked up, pelleted and activated as described before. Analysis showed the catalyst to contain 1.1 mols of phosphorus per mol of vanadium.

In the catalytic air oxidation of n-butane this catalyst had a $K_{800}$ value of 2900 and a selectivity of 56% after 318 hours on stream.

EXAMPLE 8

A flask was charged with 154.5 grams (0.85 mol) of vanadium pentoxide, 75 grams (0.17 mol) of tantalum pentoxide, 400 ml. of isobutyl alcohol and 200 ml. of benzyl alcohol. This mixture was heated at reflux for 22 hours. At the end of this time it was cooled to room temperature and 200 g. (2.04 mol) of 100% orthophosphoric acid in 400 ml. of isobutyl alcohol was added carefully. Then the resulting mixture was heated at reflux for 20 hours. After cooling to room temperature, the solid product was separated from the liquid medium by filtration. The product cake contained 19% by weight of filtrate. It was extruded in the form of ⅛" by ¼" pellets, which were dried by heating for 2 hours at 150° C. They were then activated by the usual procedure and then used as a catalyst for the air oxidation of n-butane. After 576 hours on stream, the activity value of $K_{800}$ was 4700 and the selectivity was 56 mol %. The surface area was measured by the BET method to be m²/gram and the average vanadium oxidation state was +4.4.

EXAMPLE 9

Other catalysts were prepared by the procedure of example 8, except that the tantalum oxide was replaced by an equal molar amount of other metal salts. The results are as follows:

| Ex. 9 | Metal Salt | Surface Area (m²/g) | Vanadium Oxidation State | $K_{800}$ | Selectivity |
|---|---|---|---|---|---|
| a | Titanium dioxide | 46 | +4.17 | 2900 | 49 |
| b | Niobium pentoxide | 9 | +4.5 | 1300 | 43 |
| c | Antimony trioxide | 16 | | 1100 | 21 |
| d | Bismuth trioxide | 21 | +4.3 | 3900 | 51 |
| e | Chromium trioxide | 21 | | 3200 | 57 |

As shown by Examples 8 and 9, catalysts containing elements other than vanadium, phosphorus and oxygen can be prepared by the present process. Such catalysts may contain up to 0.2 mols, preferably 0.1 mol, of the other element per mol of vanadium. The elements preferred for this purpose are the variable valent transition metals, although alkali or alkaline earth metals have also been used. The most preferred elements are those of Group V of the Periodic Table, especially tantalum and bismuth. Such additives are incorporated in the catalyst by simply combining the desired amount of the metal in the form of its oxide, phosphate or vanadate salt with the vanadium-containing compound in the reducing step.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

We claim:

1. A process for preparing a catalyst having an intrinsic surface area of at least 10 m²/g which is effective to catalyze the oxidation of a hydrocarbon to maleic anhydride comprising the steps of:
   (a) heating vanadium pentoxide with a substantially anhydrous unsubstituted alcohol of 1–10 carbon atoms and 1–3 hydroxyl groups, and being free of olefinic double bonds, to reduce the vanadium of the vanadium pentoxide to a valence between 4.0 and 4.6 and thereby obtain a vanadium-containing feed,
   (b) contacting an orthophosphoric acid with the vanadium-containing feed to form a heterogeneous reaction mixture of suspended vanadium(IV) phosphate,
   (c) removing liquid from the heterogeneous mixture to obtain the vanadium(IV) phosphate compound, and
   (d) calcining the vanadium(IV) phosphate compound to obtain said catalyst.

2. A process according to claim 1 wherein the alcohol is isobutanol.

3. A process according to claim 1 wherein the alcohol is a mixture of isobutanol and benzyl alcohol.

4. A process for preparing a catalyst having an intrinsic surface area of at least 10 m²/g which is effective to catalyze the oxidation of a hydrocarbon to maleic anhydride comprising the steps of:
   (a) heating vanadium pentoxide with a substantially non-corrosive anhydrous organic liquid reducing agent composed of carbon, hydrogen and oxygen which has the following properties;
      (1) contains no olefinic double bonds,
      (2) has a carbon atom content in the range from 1 to 20, and
      (3) is relatively unreactive toward phosphoric acid, to reduce the vanadium of the vanadium pentoxide to a valence between 4.0 and 4.6 and thereby obtain a vanadium-containing feed;
   (b) contacting an orthophosphoric acid with the vanadium-containing feed to form a heterogeneous reaction mixture of suspended vanadium(IV) phosphate,
   (c) removing liquid from the heterogeneous mixture to obtain the vanadium(IV) phosphate compound, and
   (d) calcining the vanadium(IV) phosphate compound to obtain said catalyst.

5. A process according to claim 4 wherein said organic liquid reducing agent is selected from the group consisting of alcohols, aldehydes, ketones, and ethers.

6. A process according to claim 4 wherein said organic liquid reducing agent comprises at least 40 volume percent of a hydroxylic organic compound.

* * * * *

UNITED STATES PATENT AND TRADEMARK OFFICE
CERTIFICATE OF CORRECTION

PATENT NO. : 4,132,670

DATED : January 2, 1979

INVENTOR(S) : Kiyoshi Katsumoto and David M. Marquis

It is certified that error appears in the above-identified patent and that said Letters Patent are hereby corrected as shown below:

Column 8, line 26, "Average bed pressure (atm.)" should read --Average bed pressure (psia)--.

Column 8, line 28, "(75°F, 1 psia.)" should read --(75°F, 1 atm.)--.

Column 12, line 8, "vandium" should read --vanadium--.

Signed and Sealed this

Fifteenth Day of May 1979

[SEAL]

Attest:

RUTH C. MASON
Attesting Officer

DONALD W. BANNER
Commissioner of Patents and Trademarks